(12) United States Patent
Yuan et al.

(10) Patent No.: US 10,801,051 B2
(45) Date of Patent: *Oct. 13, 2020

(54) BIOMASS FRACTIONATION PROCESS FOR BIOPRODUCTS

(71) Applicant: FPInnovations, Pointe-Claire (CA)

(72) Inventors: Zhirun Yuan, Pointe-Claire (CA); Thomas Carl Browne, Montreal (CA); Xiao Zhang, Richland, WA (US)

(73) Assignee: FPInnovations, St-Jean, Pointe-Claire (CA)

( * ) Notice: Subject to any disclaimer, the term of this patent is extended or adjusted under 35 U.S.C. 154(b) by 595 days.

This patent is subject to a terminal disclaimer.

(21) Appl. No.: 15/407,378

(22) Filed: Jan. 17, 2017

(65) Prior Publication Data

US 2017/0159091 A1 Jun. 8, 2017

Related U.S. Application Data (62) Division of application No. 12/926,323, filed on Nov. 10, 2010, now Pat. No. 9,580,454.

(60) Provisional application No. 61/272,875, filed on Nov. 13, 2009.

(51) Int. Cl.
| | | |
|---|---|---|
| *C12P 19/14* | (2006.01) | |
| *C08H 8/00* | (2010.01) | |
| *C12P 7/10* | (2006.01) | |
| *C12P 19/04* | (2006.01) | |
| *C12P 17/06* | (2006.01) | |
| *C13K 1/02* | (2006.01) | |
| *C07G 1/00* | (2011.01) | |
| *C12P 19/02* | (2006.01) | |

(52) U.S. Cl.
CPC ............... *C12P 19/14* (2013.01); *C07G 1/00* (2013.01); *C08H 8/00* (2013.01); *C12P 7/10* (2013.01); *C12P 17/06* (2013.01); *C12P 19/02* (2013.01); *C12P 19/04* (2013.01); *C13K 1/02* (2013.01); *C12P 2201/00* (2013.01); *Y02E 50/16* (2013.01)

(58) Field of Classification Search
CPC ....................................................... C12P 19/14
See application file for complete search history.

(56) References Cited

U.S. PATENT DOCUMENTS

| | | | |
|---|---|---|---|
| 3,652,387 A | 3/1972 | Wilder | |
| 4,070,232 A | 1/1978 | Funk | |
| 4,520,105 A | 5/1985 | Sinner et al. | |
| 4,612,286 A | 1/1986 | Sherman et al. | |
| 4,742,814 A | 5/1988 | Sinner et al. | |
| 5,424,417 A | 1/1995 | Torget et al. | |
| 5,730,837 A | 3/1998 | Black et al. | |
| 7,300,541 B2 | 11/2007 | Sabourin | |
| 7,381,294 B2 | 6/2008 | Suzuki et al. | |
| 7,566,014 B2 | 7/2009 | Koslow et al. | |
| 7,758,720 B2 | 7/2010 | Sabourin | |
| 7,758,721 B2 | 7/2010 | Sabourin | |
| 2003/0176669 A1 | 9/2003 | Thorre | |
| 2008/0032344 A1 | 2/2008 | Fallavolita | |
| 2008/0038784 A1 | 2/2008 | Arnaud-Taylor | |
| 2008/0057307 A1 | 3/2008 | Koslow et al. | |
| 2008/0057555 A1 | 3/2008 | Nguyen | |
| 2008/0277082 A1 | 11/2008 | Pschorn et al. | |
| 2009/0062523 A1 | 3/2009 | Malkki | |
| 2009/0151880 A1 | 6/2009 | Aichinger et al. | |
| 2009/0288789 A1 | 11/2009 | Sabourin et al. | |
| 2010/0269990 A1 | 10/2010 | Dottori | |

FOREIGN PATENT DOCUMENTS

| | | | |
|---|---|---|---|
| CA | 2368872 | 10/2000 | |
| CA | 2541229 | 9/2006 | |
| EP | 0429422 | 5/1991 | |
| WO | 00/50688 | 8/2000 | |
| WO | 2006/017655 | 2/2006 | |
| WO | 2006111604 | 10/2006 | |
| WO | 2007111605 | 10/2007 | |
| WO | 2008131229 | 4/2008 | |
| WO | 2008095098 | 8/2008 | |
| WO | WO-2009116070 A2 * | 9/2009 | ............... C12P 7/10 |
| WO | 20100029568 | 3/2010 | |

OTHER PUBLICATIONS

US Department of Energy (DOE) Report, "Biomass", Top Value Added Chemicals from Biomass vol. I: Results of Screening for Potential Candidates from Sugars and Synthesis Gas, T. Werpy et al, pp. 1-67, Aug. 2004.
PCT/CA2010/001824, International Search Report—dated Feb. 24, 2011.
EP 10829423.2, Supplementary European Search Report, dated Sep. 6, 2013.
Zhang et al. "Fractionating Recalcitrant Lignocellulse at Modest Reaction Conditions".Biotechnology and Bioengineering, vol. 97, No. 2, Jun. 1, 2007.
Communication dated Oct. 7, 2016 in corresponding EP Application 10 829 423.2.

* cited by examiner

*Primary Examiner* — Amy L Clark
(74) *Attorney, Agent, or Firm* — Norton Rose Fulbright Canada (57) ABSTRACT

A fractionation process for producing value-added products from a lignocellulosic biomass, comprises: a) mechanically refining the lignocellulosic biomass under mild refining conditions to form a refined biomass pulp with enhanced susceptibility to separation of hemicellulose, cellulose and lignin, and enhanced digestibility of carbohydrates in hydrolysis b) separating hemicellulose and sulfur-free high-quality lignin from cellulose in the refined biomass, and, optionally c) producing various bioproducts from the above said process.

14 Claims, 4 Drawing Sheets

BIOMASS FRACTIONATION PROCESS FOR BIOPRODUCTS

CROSS-REFERENCE TO RELATED APPLICATION

This application is a divisional of U.S. patent application Ser. No. 12/926,323, filed Nov. 10, 2010, now allowed, which application claims the benefit under 35 USC 119(e) of U.S. Provisional Application Ser. No. 61/272,875, filed Nov. 13, 2009.

BACKGROUND OF THE INVENTION

(i) Field of the Invention

This invention relates to a process of producing value-added bioproducts from a lignocellulosic biomass.

Lignocellulosic biomass in the invention refers to any type of plant biomass that is composed of cellulose, hemicellulose and lignin, typically in amounts of 30-55%, by weight, cellulose; 15-35%, by weight, hemicellulose; and 5-31%, %, by weight, lignin.

(ii) Description of Prior Art

Cellulose is the main structural constituent in plant cell walls. Cellulose is a carbohydrate comprising long chains of the six carbon sugar glucose that are connected end to end linearly as a polymer through β-O-4 glucosidic bonds. The long-chain cellulose is linked together by hydrogen and van der Waals bonds, which cause the cellulose to be packed into microfibrils. Hemicellulose and lignin cover the microfibrils.

Hemicellulose is a complex carbohydrate structure that consists of different polymers like pentoses (like xylose and arabinose), hexoses (like mannose, glucose, and galactose), and sugar acids. The dominant component of hemicellulose from hardwood and softwood is xylan and glucomannan, respectively.

Lignin is a complex, large heteropolymer consisting of three different phenylpropane units (coniferyl, coumaryl, and sinapyl alcohols) held together by different kinds of linkages.

Bioconversion of lignocellulosic materials to biofuel and bioproducts is a multistep process which involves the breakdown of the feedstocks followed by hydrolysis and extraction of various components. For example, bioconversion of lignocellulosic materials to biofuel (e.g. ethanol) typically consists of four main process steps: pretreatment, enzyme hydrolysis, fermentation and products recovery. There are also processes designed to extract specific components from biomass feedstock. These processes also employ a pretreatment step for the purpose of reducing the particle size of the biomass and creating large surface area for downstream processes. Pretreatment has a major impact on bioconversion process efficiency and economics. Many pretreatment techniques/methods have been developed for lignocellulosic materials using mechanical force, steam, acid, alkaline or biological agents or a combination of two or more thereof.

Mechanical refining has attracted increasing attention recently as a pretreatment for lignocellulosic biomass. Mechanical refining is an industrial process employed to produce mechanical pulp where the biomass raw materials are separated into fibres by a combination of heat and mechanical force. Several variations of mechanical pulping process are employed on an industrial scale, including refiner mechanical pulping (RMP), thermomechanical pulping (TMP), chemithermomechanical pulping (CTMP) and chemimechanical pulping (CMP). One of the major disadvantages of using mechanical pulping for a papermaking process is the high energy consumption associated with mechanical pulping, producing one ton of mechanical pulp typically requires up to 4000 kWh of electricity. The bulk of the energy consumed during refining is to develop pulp fibre while only a small fraction of the energy is directed to the actual fibre separation.

Pretreating lignocellulosic biomass using a refiner has been a subject of several recent studies. Colin et al in WO 2008/131229 A1 disclosed a method of processing lignocellulosic biomass using a combined thermochemical pretreatment and mechanical refining. The refining pretreatment was carried out at a temperature between 165° C. and 220° C., and a pressure 100 psig to 700 psig (7-48 bars or 700 to 4800 kPa), for a duration of 5 seconds to 15 minutes. The focus of Colin et al was to improve the glucose yield in a subsequent cellulose hydrolysis, for ethanol production with little discussion on the utilization of hemicellulose and lignin content of the lignocellulosic biomass. Another recent research carried out by Zhu et al (Bioresources Technology, 100(2009), 2411-2418) incorporates disk refining as a post-treatment after sulphite pulping (pretreatment) to reduce particle size of the substrate and enhance hydrolysis efficiency. A significant amount of chemicals, including 8-10% bisulfite and 1.8-3.7% sulfuric acid, were applied during sulphite pretreatment which are expected to significantly alter the nature of lignin. Pschorn et al. US 2008/0277082 A1 disclosed a high pressure compressor which is converted from a mechanical refiner and can be used for treating the biomass by a steam explosion method.

SUMMARY OF THE INVENTION

It is an object of this invention to provide a novel biomass fractionation process for producing value-added products from lignocellulosic biomass.

In accordance with one aspect of the present invention, there is provided a mechanical fractionation process for producing value-added bioproducts from a lignocellulosic biomass comprising lignin and carbohydrates, the process comprising steps of: i) mechanically refining the lignocellulosic biomass in a mechanical refiner under refining conditions to disintegrate and reduce the particle size of the lignocellulosic biomass and form a refined biomass comprising said lignin and carbohydrates, said refining conditions being carried out at a refining energy of 720 to 4320 MJ/t (200 to 1200 kWh/t) and a pressure of 100 to 600 kPa (1-6 bars); ii) enzymatically hydrolysing carbohydrates in the refined biomass to sugars to form a mass comprising a sugar fraction and a lignin fraction; iii) separating the lignin fraction from the sugar fraction, and iv) recovering said lignin fraction and recovering said sugar fraction.

In accordance with another aspect of the present invention, there is provided a process defined herein, further comprising v) fermenting said sugar fraction to form sugar bioproducts selected from biofuels, sugar alcohols and sugar acids as the products.

In accordance with another aspect of the present invention, there is provided a process according defined herein, further comprising a biological or chemical treatment.

In accordance with another aspect of the invention there is provided the process defined herein, wherein the treatment is a chemical treatment and is after step i).

In accordance with another aspect of the present invention, there is provided a process according defined herein, wherein said biomass has a particle size range 0.1 mm to 100 mm.

In accordance with another aspect of the present invention, there is provided a process defined herein wherein step ii) comprises enzymatically hydrolysing cellulose in the refined biomass to sugars.

In accordance with another aspect of the present invention, there is provided a process defined herein, wherein step i) is carried out at 1080 MJ/t to 2520 MJ/t (300 to 700 kWh/t) and 200 to 400 kPa (2 to 4 bars).

In accordance with another aspect of the present invention, there is provided a process defined herein wherein step i) is carried out at a biomass consistency of 20% to 50%.

In accordance with another aspect of the present invention, there is provided a process defined herein, wherein step i) is carried out at a biomass consistency of 20% to 50%.

In accordance with another aspect of the present invention, there is provided a process defined herein, further comprising a chemical treatment prior to step i) to produce and recover valuable bioproducts from said lignocellulosic biomass and to facilitate the separation of biomass in the subsequent fractionation process.

In accordance with another aspect of the present invention, there is provided a process defined herein, further comprising a chemical treatment prior to step i) to produce and recover valuable bioproducts from said lignocellulosic biomass and to facilitate the separation of biomass in the subsequent fractionation process.

In accordance with another aspect of the present invention, there is provided the process defined herein, further comprising a step of extracting a hemicellulose fraction from the refined biomass of step i) to leave a residual biomass containing lignin, and recovering the hemicellulose fraction as a product.

In accordance with another aspect of the present invention, there is provided the process defined herein, wherein said enzymatically hydrolyzing is at a temperature of 10° C. to 80° C.

In accordance with another aspect of the present invention, there is provided the process defined herein, wherein said enzymatically hydrolyzing is at a temperature of 10° C. to 80° C.

In accordance with another aspect of the present invention, there is provided a mechanical fractionation process for producing value-added bioproducts from a lignocellulosic biomass comprising lignin and carbohydrates, the process comprising steps of: i) mechanically refining the lignocellulosic biomass in a mechanical refiner under refining conditions to disintegrate and reduce the particle size of the lignocellulosic biomass and form a refined biomass comprising said lignin and carbohydrates, said refining conditions being carried out at a refining energy of 720 to 4320 MJ/t (200 to 1200 kWh/t) and a pressure of 100 to 600 kPa (1-6 bars); ia) biologically or chemically treating the refined biomass; ii) enzymatically hydrolysing carbohydrates in the refined biomass to sugars to form a mass comprising a sugar fraction and a lignin fraction; iii) separating the lignin fraction from the sugar fraction, and iv) recovering said lignin fraction and recovering said sugar fraction.

In accordance with another aspect of the present invention, there is provided the process described herein, wherein ia) is chemically treating the refined biomass.

In accordance with another aspect of the present invention, there is provided a process described herein, wherein step ii) comprises enzymatically hydrolysing cellulose in the refined biomass to sugars.

In accordance with another aspect of the present invention, there is provided a process described herein, wherein step i) is carried out at 1080 MJ/t to 2520 MJ/t (300 to 700 kWh/t) and 200 to 400 kPa (2 to 4 bars).

In accordance with the invention, there is provided a fractionation process for producing value-added bioproducts from a lignocellulosic biomass, comprising: a) mechanically refining the lignocellulosic biomass under mild refining conditions to form a refined biomass pulp with enhanced susceptibility to separation of hemicellulose, cellulose and lignin, and enhanced digestibility of carbohydrates in hydrolysis; and b) separating hemicellulose and sulfur-free high-quality lignin from cellulose in the refined biomass.

Preferably the process further comprises c) further recovering and producing various value-added bioproducts from extractives, hemicellulose, cellulose, and sulfur-free high-quality lignin.

In a particular advantageous aspect of the invention, there is provided a process for producing value-added bioproducts from a lignocellulosic biomass, comprising: i) mechanically refining the lignocellulosic biomass under mild refining conditions to form a refined biomass pulp, ii) extracting a hemicellulose fraction from the refined biomass pulp to leave a residual pulp containing lignin, iii) hydrolysing carbohydrates in the residual pulp to sugars, iv) separating a high-quality lignin fraction from the sugars, iv) fermenting said sugars to form biofuels such as ethanol and butanol, and v) recovering the hemicellulose fraction and the sugar alcohol as value-added products.

The lignin fraction and sugar acids produced in the fermentation can also be recovered as value-added products.

A significant aspect of this invention is that it provides a green process for lignocellulosic biomass fractionation, obtaining a highly digestible biomass and multiple bioproducts. The novel process can be easily retrofitted into existing mechanical pulp mills.

DETAILED DESCRIPTION OF THE INVENTION

The present invention relates to a novel, green fractionation and bioconversion process to convert lignocellulosic biomass to bioproducts and biofuel.

Lignocellulosic biomass in the invention refers to any type of plant biomass that is composed of cellulose, hemicellulose and lignin, typically in amounts of 30-55%, by weight, cellulose; 15-35%, by weight, hemicellulose; and 5-31%, by weight, lignin.

The present invention provides a green bioconversion process to convert lignocellulosic biomass to multiple bioproducts and biofuels by using a low-pressure refiner with minimum refining energy and few chemicals. It was unexpected that one could employ low energy refining conditions to provide effective pretreatment of lignocellulosic biomass.

The present invention provides a novel bioconversion process to convert lignocellulosic biomass to bioproducts and biofuel, which process comprises low-pressure mechanical refining, hemicellulose extraction, enzymatic hydrolysis, sugar/lignin separation, and fermentation. This method provides high biofuel yields and produces multiple products from the lignocellulosic biomass. This is also a green bioconversion process with minimum refining energy and few chemicals, which will produce sulfur-free high-quality lignin and value-added bioproducts.

The process employs low-pressure mechanical refining as a fractionation method to disintegrate biomass feedstock. The refining is operated under mild conditions using minimum energy input to disintegrate lignocellulosic feedstock and facilitate the separation and fractionation of hemicelluloses, cellulose and lignin in subsequent process steps. The refining conditions of the present invention also greatly enhance the digestibility of carbohydrates in the biomass by enzymatic hydrolysis whereby a high sugar yield can be obtained. If desired, the biomass could be subjected to a chemical treatment prior to the mechanical refining to obtain valuable anti-oxidants and to facilitate the separation of the biomass in the subsequent fractionation process.

The carbohydrates digested by the enzymatic hydrolysis may comprise the hemicelluloses and celluloses. If the hemicelluloses have been previously separated from the biomass the carbohydrates for digestion comprise the celluloses and any residual hemicelluloses which escape the earlier separation step.

Hemicellulose can be extracted from the pretreated substrate by either a biological or chemical agent, and further processed to high value bioproducts. After hemicellulose extraction and a subsequent hydrolysis, the remaining substrate residue contains a high percentage of lignin which can be recovered and further purified to produce high-quality lignin products. Compared to traditional kraft lignin and steam-explosion lignin, the high-quality lignin produced from this invention has little degradation, resembles the native lignin, and contains little inorganic impurities (e.g. sulfur free). The novel bioconversion process disclosed in this invention is significantly different from previous processes where steam explosion (high temperature and pressure; ≥165° C. and 700 kPa) is used to reduce the particle size of the biomass. The present process can be considered a "green" bioconversion process which fractionates lignocellulosic biomass using a combined low pressure (100-600 kPa) and a minimum refining with no or few chemicals. This green, multiple-step process could be used to produce multiple products and native components from biomass such as sulfur-free high-quality lignin.

DETAILED DESCRIPTION WITH REFERENCE TO THE DRAWINGS

The concept of the present invention can be illustrated by reference to FIG. 1.

Lignocelulosic biomass is first subjected to mechanical refining at a set of conditions (temperature, pressure, time etc). If desired, the biomass could be subjected to a chemical treatment to obtain valuable anti-oxidants and to facilitate the separation of biomass in the subsequent fractionation process. The treated substrates are collected as pulp from the mechanical refining. The hemicellulose can be extracted from the pulp in either polymeric or oligomeric form by using chemical or biochemical methods. The polymeric hemicellulose fractions can be used as papermaking additives while the oligomeric hemicellulose fractions can be applied as functional food for human and animal consumption. Other applications of hemicellulose fractions are also possible. Extraction of hemicellulose from the pulp is found to enhance the digestibility of cellulose in the pulp to enzyme hydrolysis. Cellulase enzyme, for example, will convert cellulose to glucose which can then be processed to various products, including sugar alcohols, sugar acids and biofuels. The hydrolysis of carbohydrates results in a substrate residue which contains primarily lignin. Since few chemicals are employed in the process, the lignin thus produced is of low inorganic impurity and sulfur free. The property of this high-quality lignin is similar to that of the native lignin, which affords its potential for high value applications.

Figure 1:
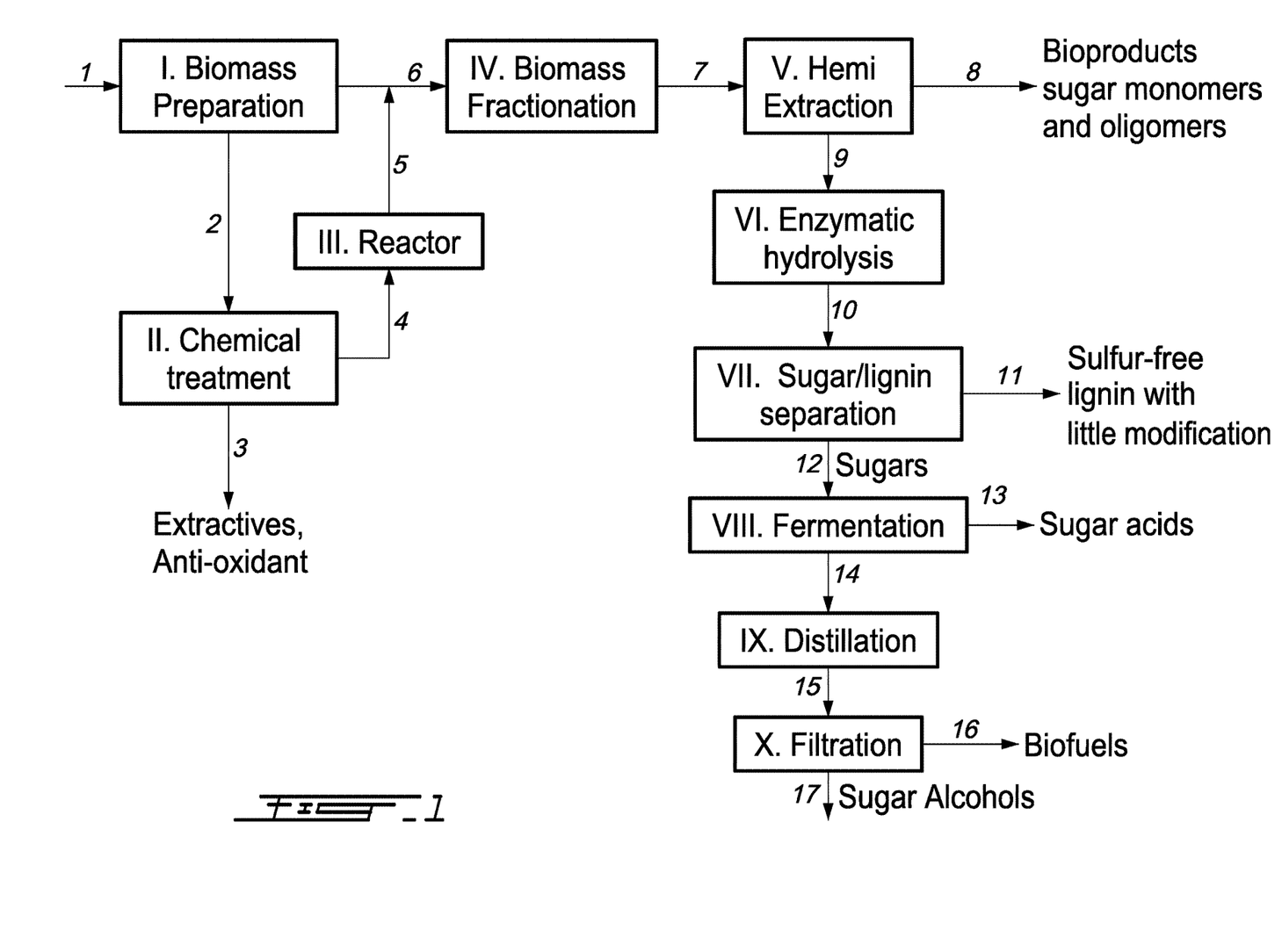
FIG. 1 illustrates schematically a process of the invention.

With particular reference to FIG. 1, lignocellulosic biomass 1 refers to any type of plant biomass that is composed of, in wt %, cellulose (30-55%), hemicellulose (15-35%), and lignin (5-31%).

The novel process may generally comprise the following steps:

I. Preparation

The lignocellulosic biomass 1 is to be washed and drained before further processing. The particle size of the biomass material 2 varies widely and depends on the type of biomass used. In general, the particle size may range from less than a millimeter to centimeters in length, for example 0.1 mm to 100 mm. In the case of wood, the chips from commercial chippers may be suitable. By way of example the wood chip size may typically be 15-25 mm long and 2-5 mm thick.

II. Chemical Treatment

If desired, the biomass is subjected to a chemical treatment to obtain valuable extractives, in particular anti-oxidants 3 and to facilitate the separation of biomass in the subsequent fractionation process by decreasing the chemical bonds among cellulose, hemicellulose, and lignin. A press impregnator may be used to press out the extractives and other valuable bioproducts such as flavonoids (antioxidant) before or after the pre-treatment. A high volume compression ratio (4:1 or higher) could be achieved using the press impregnator to achieve uniform and quick penetration of the treatment chemicals. Mild acids and alkali, enzymes, oxidants, and other chemicals may be used. Temperatures below 100° C. are preferred. Mild chemicals include but are not limited to acetic acid, dilute sulfuric acid, hydrochloric acid, sodium hydroxide, hydrogen peroxide, etc. The treated biomass 4 needs less mechanical force to reduce its particle size, as compared with biomass which has not been treated.

Figure 2:
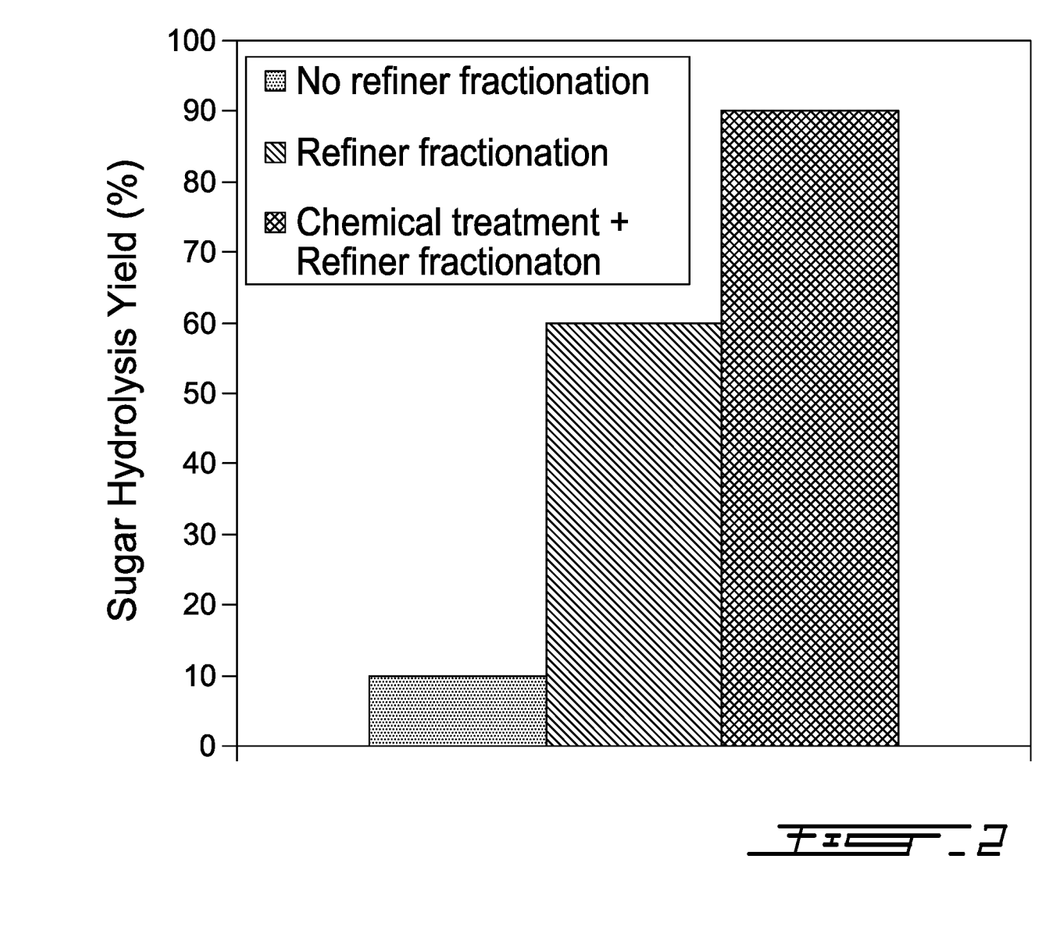
FIG. 2 shows graphically the improved hydrolysability of the glucose and xylose of various biomass following refiner fractionation with and without chemical treatment.

FIG. 2 shows graphically the improved hydrolysability of the carbohydrates of various biomass following refiner fractionation with and without chemical treatment. The hydrolysis was done at 50° C., pH 4.8, 2% consistency and with a mixture of cellulase and xylanase.

The flavonoids are a class of plant polyphenols which share the common structure of diphenylpropanes ($C_6$—$C_3$—$C_6$). Over 4000 different types of flavonoids have been identified including quercetin, chalcone, flavone, flavanol, flavanone, anthocyanin, catechin, biflavonoid and condensed tannins (polymeric forms of flavonoids such as proanthocyanidins). Numerous studies have shown that flavonoids can improve human health and fight different diseases to various degrees. For example, quercetin has been reported to block the "sorbitol pathway" which is believed to be associated with diabetes. As an antioxidant, the ability of proanthocyanidin to prevent oxidative damage on LDL cholesterol has been well demonstrated. Antioxidants are compounds that protect cells against the damaging effects of reactive oxygen species, such as singlet oxygen, superoxide, peroxyl radicals and hydroxyl radicals.

The present invention as illustrated in FIG. 1 allows for the recovery of these valuable products from the biomass.

III. Reactor

If a chemical treatment II is used, then a reactor III as reaction vessel may be required. Temperatures for the chemical treatment may typically be in the range of 20 to 145° C. for 1 to 30 minutes. The mild reaction conditions (low temperature and short retention time) have a minimum impact on the natural hemicellulose and lignin of the biomass.

IV. Fractionation

The fractionation process employs a mechanical refiner to first disintegrate the biomass feedstock, either pre-treated 5 or not pre-treated 6. Mechanical refiners use mechanical force and heat to reduce the particle size of the biomass in order to expose more surface area for the subsequent treatments including hemicellulose extraction and enzymatic hydrolysis of carbohydrates. The refining is operated at mild conditions using minimum energy input to disintegrate lignocellulosic feedstock and facilitate the separation and fractionation of hemicelluloses, cellulose and lignin in subsequent processes. The refining energy may suitably be 720 to 4320 MJ/t (200 to 1200 kWh/t) and refining pressure of 100 to 600 kPa (1 to 6 bars). Preferably the refining energy and pressure are 1080 MJ/t to 2520 MJ/t (300 to 700 kWh/t) and 200 to 400 kPa (2 to 4 bars), respectively. The refining consistency can be between 20 to 50%. Chemicals or biochemicals such as enzymes, alkaline peroxide, or others frequently found in pulp mills may be added before or in the refiner to help facilitate the subsequent fractionation processes. The refining conditions disclosed in this invention also greatly enhance the digestibility of carbohydrates in enzymatic hydrolysis whereby high sugar yields can be obtained.

Figure 3:
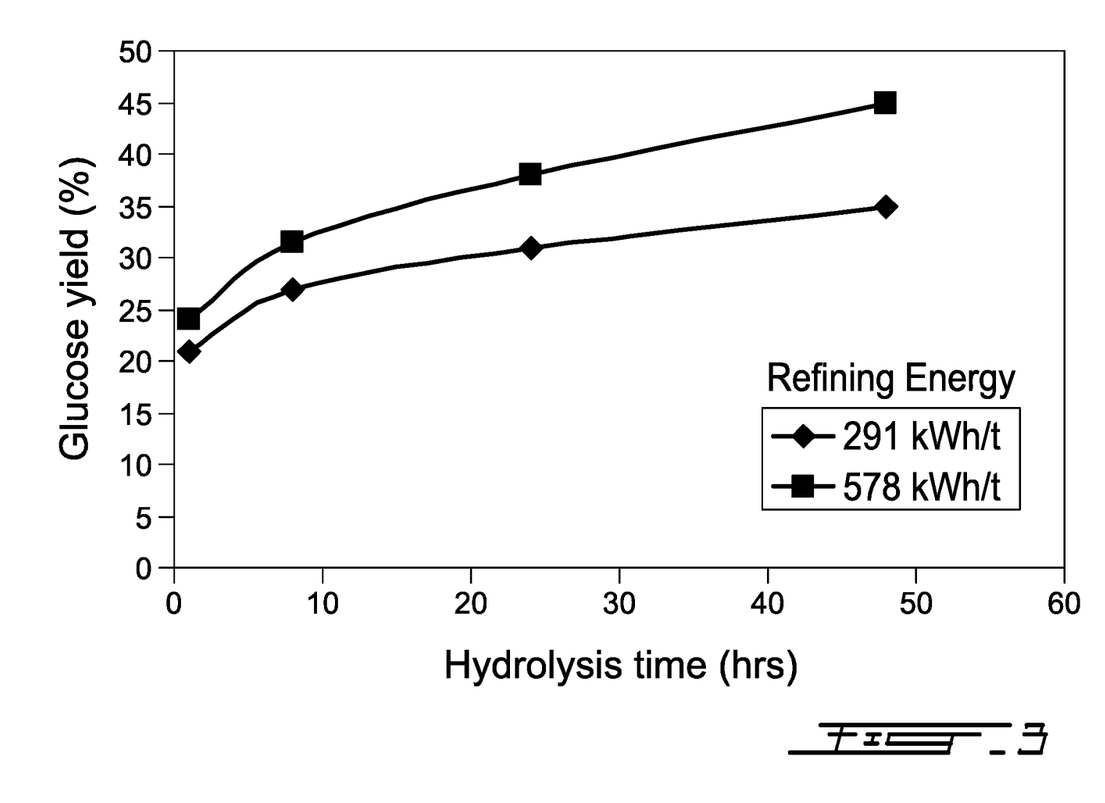
FIG. 3 shows graphically the relationship between glucose yield and hydrolysis time for refined biomass pulps produced at different refining energies under the mild refining conditions of the invention.

FIG. 3 shows the glucose yield during hydrolysis for the biomass refined at two different energy levels with an atmospheric refiner. The higher the refining energy, the higher the glucose yields. The hydrolysis was done at 50° C., pH 4.8, 2% consistency and with cellulase.

The novel bioconversion process disclosed in this invention is significantly different from previous bioconversion processes where, for example, steam explosion is used to reduce size of biomass. The present invention provides a "green" bioconversion process to fractionate lignocellulosic biomass using a combined low pressure and a minimum refining with no or few chemicals. This green, multiple-step process can be used to produce multiple products and native components from the biomass such as sulfur-free high-quality lignin.

V. Hemicellulose Extraction

Figure 4:
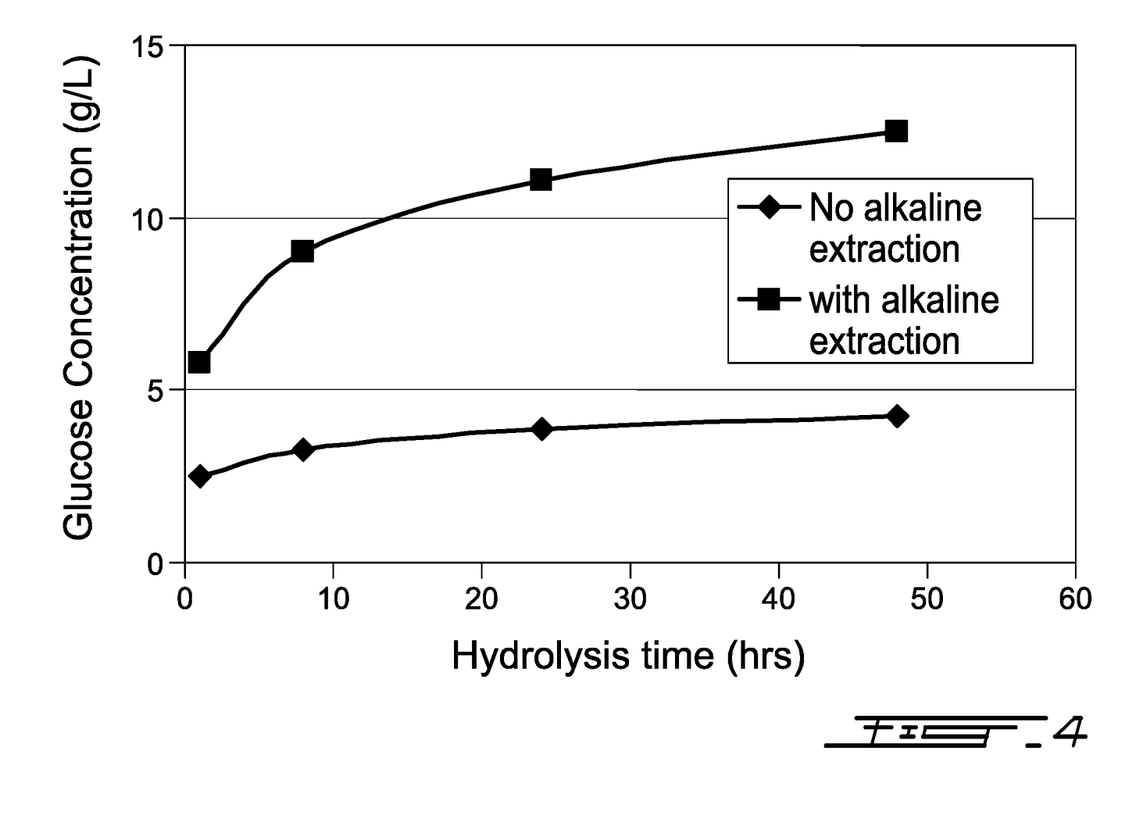
FIG. 4 shows graphically the improved hydrolysability of the cellulose of the refined biomass pulp, following extraction of a hemicellulose fraction of the pulp.

Hemicellulose can be extracted from the fractionated substrate 7 by either biological or chemical agents, and further processed to sugar monomers and oligomers, see for example pathways described in the US Department of Energy (DOE) report, "Biomass", Top Value Added Chemicals from Biomass Volume I—Results of Screening for Potential Candidates from sugars and Synthesis Gas, T. Werpy et al, Pages 1 to 67, August 2004, incorporated herein by reference. The extraction process may be at 10-80° C. for 5 to 240 minutes, using alkali, mild acid, solvent, or a combination of these chemicals. The hemicellulose 8 can be extracted from the pulp in either polymeric or oligomeric form: the polymeric hemicellulose fractions can be used as papermaking additives while the oligomeric hemicellulose fractions can be applied as functional food for human and animal consumptions. Extraction of hemicellulose from the pulp also enhances the digestibility of cellulose to enzyme hydrolysis. As shown in FIG. 4, the alkaline extraction of hemicellulose improved the hydrolysability of the cellulose in the refined biomass.

A reaction vessel and a press can be used to extract and separate the hemicellulose from the remaining biomass which mainly contains cellulose and lignin.

VI. Enzymatic Hydrolysis

The remaining biomass after hemicellulose extraction is subjected to enzymatic hydrolysis. Cellulolytic enzymes and/or other enzymes may be used to convert carbohydrates to sugars which can then be processed to various products, including sugar alcohols, sugar acids and biofuels. The hydrolysis may suitably be carried out at a pH between 3 to 9, 10-80° C., 2-30% consistency for up to 144 hours. High-consistency (up to 30%) hydrolysis is preferred to increase the concentration of sugars. Hydrolysis yield above 95% can be obtained.

VII. Sugar/Lignin Separation

After hemicellulose extraction and carbohydrate, mainly cellulose, hydrolysis, the remaining substrate residue 10 contains a high percentage of lignin which can be further extracted or purified to produce high-quality lignin products 11. Since few chemicals and mild conditions are employed in the process, the high-quality lignin produced from this invention has little degradation, resembles the native lignin, and contains little inorganic impurity (e.g. sulfur free) as compared with kraft lignin and steam-explosion lignin. Table 1 shows that the lignin extracted from the present invention resembles the native wood lignin as represented by the ball-milled wood lignin (Granata et al., J. Agric Food Chem. 1995, 43, 1538-1544), which affords its potential for high-value applications. Compared to the ball-milled wood lignin, the lignin from steam explosion or Alcell™ process has much more degradation due to the severe process conditions.

TABLE 1

Comparison of extracted lignin from various sources

|  | Total phenolic —OH mmoles/g lignin | Total Aliphatic —OH mmoles/g lignin |
| --- | --- | --- |
| Steam Explosion | 2.47 | 3.53 |
| Alcell ™ Organosolv | 4.32 | 1.74 |
| Ball Milled | 1.05 | 6.21 |
| Present Invention | 0.73 | 6.34 |

Filtering, pressing, solvent extraction, or membrane technology can be used to separate sugars 12 from lignin 11.

VIII. Fermentation

Fermentation is suitably carried out under 70° C. for up to 3 days. After distillation and filtration, the potential products are biofuels 16, sugar acids 13, and sugar alcohols 17.

BENEFIT OF INVENTION

The forest biorefinery concept is the one where a series of processes are used to take wood apart into its constituent components and make the most value of each one. The current forestry model, of making lumber from the logs, paper from the residual material left over from sawmills, and heat and power from the sawdust and bark, is an example of a forest biorefinery. Unfortunately lumber and paper are no longer valuable enough to sustain a viable industry, and it is unclear if or when this situation will reverse.

The newsprint market has been declining over the years and a large number of mills have been shut down. Also mills are forced to cut down productions, and, therefore, are now or will soon be in the position of having excess pulp production capacity, and the corresponding excess wood supply. Furthermore, paper mills usually have access to low grade wood supplies which cannot profitably be converted to either lumber or paper. It is important, therefore, to find new uses of and products from the forest (which is the one asset that will not go away), ideally by reusing existing industrial assets with little capital investment.

The current invention may use a large part of mill existing feedstock and equipment with little capital investment. The following demonstrates the economics of the process of the invention, subject to the research activities which may change theses numbers.

The process of the invention may be expected to extract of the order of 150 kg of hemicellulose from each tonne of wood processed. Potential end uses include furfural, xylose or glucose (depending on wood supply) or other plastics precursors. The value of furfural in 2009 is $1250 per tonne; at a 50% conversion rate of the hemicellulose, revenues of $100 might be expected for each 150 kg of hemicellulose extracted from each tonne of wood. Other very high value products, such as xylo-oligomers, can generate 2009 prices as high as $25,000 per tonne; whereby revenues of $1250 for a 50 kg stream are possible.

Most of the cellulose and most of the remaining hemicellulose will be converted to sugars for fermentation. Converting of the order of 450 kg of mainly cellulose will yield about 280 litres of ethanol. At $0.50 per litre this represents revenues of $140 for the 450 kg of wood converted. Capital required, apart from modifications to the TMP plant, is for fermentation and distillation.

The process of the invention may generate approximately 200 kg of high-quality lignin. Unlike most industrial lignin preparations (e.g. kraft lignin, lignosulfonate), this high-quality lignin will maintain the original structure and chemical characteristics of native lignin. The uses of kraft lignin include resins to replace phenol-formaldehyde resins (which are about to be banned in California), replacement for carbon black in tires, etc. Various products may take advantage of the unique properties of this high-quality lignin. The invention thus offers a green alternative to a product such as carbon black at $1500/t, and all fractions of lignin can be used for various products, thereby providing potential revenues of the order of $300 for the lignin stream. Requirements will include separation equipment (e.g. belt press, membrane) to separate glucose streams from lignin.

Total yield is thus 80%. Potential revenues from a tonne of wood are thus of the order of $400 to $2100. Higher fractionation and conversion efficiencies increase the yield and thus the revenues.

The thermomechanical pulping plant will generate very little steam at the low energy level employed, and the fermentation plant will require steam, so having a bark boiler onsite for steam generation may be appropriate. Table 2 below is a summary of the potential value that could be obtained from a tonne of wood.

| Name of wood component | Mass (kg) | Product | Mass/volume | Price | Value ($) |
|---|---|---|---|---|---|
| Cellulose | 450 | Ethanol | 280 L | $0.5/L | 140 |
| Lignin | 200 | bioproducts | 200 kg | $0.4-1.5/kg | 80-300 |
| Hemi-cellulose | 150 | Furfural/xylitol | 150 kg | $1.2-3/kg | 180-450 |
|  |  | Xylo-oligomers | 50 kg | $33/kg | 1650 |
| Total |  |  |  |  | 400-2100 |

Table 3 below is a summary of typical mild process conditions for the different stages of the process of the invention:

| Unit operation | Conditions |
|---|---|
| Chemical treatment | Mild chemicals + press impregnation |
| Reaction | 20-145° C. (up to 400 kPa), 1-30 min |
| Refining Fractionation | Low-pressure refining, 100-600 kPa, 720-4320 MJ/t |
| Hemicellulose extraction | Mild chemicals + press impregnation, 10-80° C., 5-180 min |
| Enzymatic Hydrolysis of Cellulose | 10-80° C., 2-30% conc., 3-144 hrs, close to neutral pH |
| Sugars/lignin separation | Filtering, pressing, membrane |
| Fermentation of sugars | <70° C. |

Particular benefits of the process of the invention include that it has a great potential in terms of the following:
a. A novel green process using mild process conditions with emphasis on producing various bioproducts from biomass
b. Can be easily retrofitted into an existing mechanical pulp mill
c. Very high hydrolysis yield and concentrated sugar stream
d. High-quality sulfur-free lignin as demonstrated in Table 1 above. The lignin recovered is even better than the milled wood lignin. The extraction yield of 40-50% of original lignin in wood is also excellent.
e. There is also a potential to extract hemicellulose after refining for value-added bioproducts and further facilitate the hydrolysis and lignin extraction.

Unless indicated otherwise amounts % herein are by weight; and the unit "t" refers to tonnes.

The invention claimed is:
1. A mechanical fractionation process for producing lignin and sugar from a lignocellulosic biomass comprising lignin and carbohydrates, the process comprising the steps of:
   i) mechanically refining the lignocellulosic biomass in a mechanical refiner under refining conditions to disintegrate and reduce the particle size of the lignocellulosic biomass and form a refined biomass comprising said lignin and carbohydrates, said refining conditions being carried out at a refining energy of 720 to 4320 MJ/t (200 to 1200 kWh/t) and a pressure of 100 to 600 kPa (1-6 bars);
   ii) enzymatically hydrolysing carbohydrates in the refined biomass to sugars to form a mass comprising a sugar fraction and a lignin fraction;
   iii) separating the lignin fraction from the sugar fraction, and
   iv) recovering said lignin fraction and recovering said sugar fraction.
2. The process according to claim 1, further comprising v) fermenting said sugar fraction to form sugar bioproducts selected from biofuels, sugar alcohols and sugar acids.

3. The process according to claim 1, further comprising a step of biological or chemical treatment of the lignocellulosic biomass.

4. The process of claim 3, wherein the treatment is a chemical treatment and is after step i).

5. The process according to claim 1, wherein said lignocellulosic biomass has a particle size range 0.1 mm to 100 mm.

6. The process according to claim 1, wherein step ii) comprises enzymatically hydrolysing cellulose in the refined biomass to sugars.

7. The process according to claim 1, wherein step i) is carried out at 1080 MJ/t to 2520 MJ/t (300 to 700 kWh/t) and 200 to 400 kPa (2 to 4 bars).

8. The process according to claim 1, wherein step i) is carried out at a biomass consistency of 20% to 50% by weight.

9. The process according to claim 7, wherein step i) is carried out at a biomass consistency of 20% to 50% by weight.

10. The process according to claim 1, further comprising a chemical treatment prior to step i) to facilitate the separation of the refined biomass in the subsequent hydrolyzing and separating steps.

11. The process according to claim 4, further comprising a chemical treatment prior to step i) to facilitate the separation of the refined biomass in the subsequent hydrolyzing and separating steps.

12. The process of claim 9, further comprising a step of extracting a hemicellulose fraction from the refined biomass of step i) to leave a residual biomass containing lignin, and recovering the hemicellulose fraction as a product.

13. The process of claim 1, wherein said enzymatically hydrolyzing is at a temperature of 10° C. to 80° C.

14. The process of claim 4, wherein said enzymatically hydrolyzing is at a temperature of 10° C. to 80° C.

* * * * *